US012742734B2

(12) United States Patent
Lee et al.

(10) Patent No.: US 12,742,734 B2
(45) Date of Patent: Sep. 22, 2026

(54) DIAGNOSIS SYSTEM USING FLUORESCENCE INFORMATION AND ACIDITY INFORMATION AND DIAGNOSIS METHOD USING SAME

(71) Applicant: OSONG MEDICAL INNOVATION FOUNDATION, Cheongju-si (KR)

(72) Inventors: Seung Rag Lee, Sejong (KR); Byung Jun Park, Sejong (KR); Byung Yeun Kim, Cheongju-si (KR); Young Jae Won, Sejong (KR)

(73) Assignee: OSONG MEDICAL INNOVATION FOUNDATION, Cheongju-si (KR)

( * ) Notice: Subject to any disclaimer, the term of this patent is extended or adjusted under 35 U.S.C. 154(b) by 395 days.

(21) Appl. No.: 18/281,583

(22) PCT Filed: Mar. 18, 2022

(86) PCT No.: PCT/KR2022/003859

§ 371 (c)(1),
(2) Date: Sep. 12, 2023

(87) PCT Pub. No.: WO2022/203295

PCT Pub. Date: Sep. 29, 2022

(65) Prior Publication Data

US 2024/0151648 A1 May 9, 2024

(30) Foreign Application Priority Data

Mar. 25, 2021 (KR) ........................ 10-2021-0038694

(51) Int. Cl.
*G01N 21/64* (2006.01)
*G01N 33/483* (2006.01)
(Continued)

(52) U.S. Cl.
CPC ..... *G01N 21/6486* (2013.01); *G01N 33/4833* (2013.01); *G01N 33/487* (2013.01); *G16H 50/20* (2018.01)

(58) Field of Classification Search
CPC ............. G01N 21/6408; G01N 21/645; G01N 21/6458; G01N 21/6486; G01N 33/4833;
(Continued)

(56) References Cited

U.S. PATENT DOCUMENTS

2011/0224513 A1 9/2011 Adachi et al.
2011/0320174 A1* 12/2011 Ragan ................ G01N 21/6408 702/189
2022/0198787 A1* 6/2022 Tizhoosh .............. G06F 16/532

FOREIGN PATENT DOCUMENTS

JP 2007186492 A 7/2007
JP 2010273632 A 12/2010
(Continued)

OTHER PUBLICATIONS

International search report issued on Jun. 20, 2022.
(Continued)

*Primary Examiner* — Jennifer Wecker
(74) *Attorney, Agent, or Firm* — LEEPI

(57) ABSTRACT

In a diagnosis system using fluorescence information and acidity information and a diagnosis method using the same, the diagnosis system includes a fluorescence information obtainment part, an acidity information obtainment part, a derivation part, an acidity information calculation part and a diagnostic part. The fluorescence information obtainment part is configured to obtain fluorescence information from a sample and a specimen subject to diagnosis. The acidity information obtainment part is configured to obtain acidity information from the sample. The derivation part is configured to derive a correlation between the fluorescence information and the acidity information. The acidity information calculation part is configured to calculate acidity information of the specimen based on the fluorescence information obtained from the specimen, using the correlation. The diagnostic part is configured to perform cancer diagnosis on the specimen based on the fluorescence information obtained from the specimen and the calculated acidity information.

1 Claim, 5 Drawing Sheets

(51) Int. Cl.
*G01N 33/487* (2006.01)
*G16H 50/20* (2018.01)

(58) Field of Classification Search
CPC .. G01N 33/487; G01N 33/575; G01N 33/582; G16H 50/20
See application file for complete search history.

(56) References Cited

FOREIGN PATENT DOCUMENTS

| | | | |
|---|---|---|---|
| JP | 2011185843 | A | 9/2011 |
| JP | 2011185844 | A | 9/2011 |
| JP | 2015-34809 | A | 2/2015 |
| JP | 2019517006 | A | 6/2019 |
| KR | 20140083881 | A | 7/2014 |
| KR | 101629576 | B1 | 6/2016 |
| KR | 101913957 | B1 | 10/2018 |

OTHER PUBLICATIONS

Extended European Search Report issued on Jan. 27, 2025.

"Cancer discrimination based on real-time AMD(Analog Mean Delay)•FLIM(Fluorescence Lifetime Imaging Microscopy)", Jooran Lee et. al., Optical Diagnostics and Sensing XIX: Toward Point-of-Care Diagnostics, edited by Gerard L. Cote, Proc. of SPIE vol. 10885, 1088514.

"Near-Infrared Fluorescence Lifetime pH-Sensitive Probes", Mikhail Y. Berezin et al., Biophysical Journal vol. 100 Apr. 2011 2063-2072, pp. 2063.

Japanese patent application office action issued on Aug. 22, 2024.

Chinese application office action dated on Apr. 18, 2026.

Moinuddin Hassan, Jason Riley, Victor Chernomordik, Paul Smith, Randall Pursley, Sang Bong Lee, Jacek Capala, and Amir H. Gandjbakhche, "Fluorescence Lifetime Imaging System for In Vivo Studies", Molecular Imaging, vol. 6, No. 4 (Jul.-Aug. 2007): pp. 229-236.

* cited by examiner

DIAGNOSIS SYSTEM USING FLUORESCENCE INFORMATION AND ACIDITY INFORMATION AND DIAGNOSIS METHOD USING SAME

BACKGROUND OF THE INVENTION

Technical Field

Exemplary embodiments of the present invention relate to a diagnosis system using fluorescence information and acidity information and a diagnosis method using the same. More particularly, exemplary embodiments of the present invention relate to a diagnosis system using fluorescence information and acidity information and a diagnosis method using the same capable of performing diagnosis such as cancer diagnosis, by obtaining acidity information based on measured fluorescence information, based on a correlation between the fluorescence information and the acidity information.

Discussion of the Related Art

As the occurrence of cancer diseases increases, various cancer diagnosis technologies are being developed. In particular, recently, interest in technologies for diagnosing cancer non-invasively or using minimally invasive surgery is increasing.

In particular, in the case of non-invasive methods or minimally invasive surgeries, the quality of life after diagnosis or treatment can be improved and complications can be minimized, so the demand for related technologies is increasing. However, cancer diagnosis technology using this method has limitations in that the accuracy of diagnosis is not high.

For example, Korea Patent No. 10-1467482 discloses a cancer diagnosis technology using breathing gas as a non-invasive method, but in the case of cancer diagnosis using breathing gas, the accuracy of diagnosis is not high, so it is rarely used in practice. Accordingly, there is a need for the development of cancer diagnosis technology that can accurately diagnose each type of cancer, have high diagnostic accuracy, and relatively improve patient convenience.

As explained above, the related prior art is Korean Patent No. 10-1467482.

SUMMARY

Exemplary embodiments of the present invention provide a diagnosis system using fluorescence information and acidity information, capable of performing diagnosis such as cancer diagnosis, by obtaining acidity information based on measured fluorescence information, based on a correlation between the fluorescence information and the acidity information.

Exemplary embodiments of the present invention also provide a diagnosis method using the diagnosis system.

According to one aspect of the present invention, the diagnosis system includes a fluorescence information obtainment part, an acidity information obtainment part, a derivation part, an acidity information calculation part and a diagnostic part. The fluorescence information obtainment part is configured to obtain fluorescence information from a sample and a specimen subject to diagnosis. The acidity information obtainment part is configured to obtain acidity information from the sample. The derivation part is configured to derive a correlation between the fluorescence information and the acidity information. The acidity information calculation part is configured to calculate acidity information of the specimen based on the fluorescence information obtained from the specimen, using the correlation. The diagnostic part is configured to perform cancer diagnosis on the specimen based on the fluorescence information obtained from the specimen and the calculated acidity information.

In an exemplary embodiment, the diagnosis system may further include a storage part configured to store the correlation derived from the derivation part.

In an exemplary embodiment, the fluorescence information may include fluorescence intensity information and fluorescence lifetime information.

In an exemplary embodiment, the fluorescence lifetime information may be obtained by directly measuring a fluorescence lifetime from a detected light, using a digitizer which samples a frequency over a gigabyte.

In an exemplary embodiment, the derivation part may be configured to derive the correlation between the fluorescence lifetime information among the fluorescence information and the acidity information. The acidity information calculating part may be configured to calculate the acidity information of the specimen based on the fluorescence lifetime information among the fluorescence information obtained from the specimen.

In an exemplary embodiment, the diagnostic part may be configured to perform cancer diagnosis on the specimen based on the fluorescence intensity information and the acidity information.

In an exemplary embodiment, the fluorescence information obtainment part may be a confocal scanning system using a pulse laser. The acidity information obtainment part may be configured to obtain acidity information on the sample, based on the correlation between acidity of fluorescent contrast agent and the fluorescence information.

In an exemplary embodiment, the sample may be cancer cells of each type that are the target of diagnosis. The derivation part may be configured to derive the correlation between the fluorescence information for each type cancer cell and the acidity information.

In an exemplary embodiment, the acidity information calculation part may be configured to calculate the acidity information of the specimen, using the correlation on the cancer cell corresponding to the specimen among the derived correlation from the derivation part.

According to another aspect of the present invention, in the diagnosis method, information on a correlation between fluorescence information and acidity information is stored. The fluorescence information is obtained from a specimen subject to diagnosis. The acidity information of the specimen is calculated based on the fluorescence information obtained from the specimen, using the correlation. Cancer diagnosis on the specimen is performed based on the fluorescence information obtained from the specimen and the calculated acidity information.

In an exemplary embodiment, in the storing the information on the correlation between the fluorescence information and the acidity information, the fluorescence information may be obtained from a sample. The acidity information may be obtained from the sample. The correlation between the fluorescence information and the acidity information may be derived.

In an exemplary embodiment, in the storing the information on the correlation between the fluorescence information and the acidity information, the information on the correlation between cancer cells of each type may be stored as a sample. In calculating the acidity information, the correlation for the cancer cell corresponding to the specimen may be used among the correlation.

According to exemplary embodiments of the present invention, cancer diagnosis may be performed based on a sample by simultaneously using fluorescence information, especially fluorescence intensity information and acidity information, and thus the accuracy of cancer diagnosis may be improved compared to cancer diagnosis techniques that simply use fluorescence intensity information.

Here, considering the difficulty in obtaining acidity information for samples using a non-invasive method, various types of cancer cells that are subject to diagnosis are sampled and information on the correlation between fluorescence lifetime information and acidity information was collected in each sample, and in the case of actual samples, only fluorescence lifetime information is obtained and the acidity information is calculated based on this, and thus using the non-invasive method, user's convenience may be improved and cancer diagnosis may be performed more accurately.

In addition, the fluorescence information, that is, the fluorescence lifetime information and the fluorescence intensity information, are acquired using a confocal scanning system using a pulse laser, and thus the accuracy of information obtained may be improved, and non-invasive information acquisition may be possible, improving user's convenience.

In obtaining the fluorescence lifetime information, conventionally the optical signal obtained from the optical detector is electrically passed through a filter (GLPF, Gaussian low pass filter) and amplifier and then the signal is measured and restored at the digitizer to simplify acquisition. However, in the present example embodiment, by using the digitizer that can sample a relatively high frequency of 1 gigabyte or more, the fluorescence lifetime may be obtained by measuring the fluorescence lifetime directly from the detected light, omitting filters and amplifiers, and thus signal-to-noise ratio (SNR) may be decreased.

REFERENCE NUMERALS

- 10: diagnosis system 100: fluorescence information obtainment part
- 200: acidity information obtainment part 300: derivation part
- 400: storage part 500: acidity information calculation part
- 600: diagnostic part

DETAILED DESCRIPTION OF THE INVENTION

The present invention is described more fully hereinafter with reference to the accompanying drawings, in which exemplary embodiments of the present invention are shown. The present invention may, however, be embodied in many different forms and should not be construed as limited to the exemplary embodiments set forth herein. Rather, these exemplary embodiments are provided so that this disclosure will be thorough and complete, and will fully convey the scope of the present invention to those skilled in the art.

The terminology used herein is for the purpose of describing particular exemplary embodiments only and is not intended to be limiting of the present invention. As used herein, the singular forms "a," "an" and "the" are intended to include the plural forms as well, unless the context clearly indicates otherwise.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be explained in detail with reference to the accompanying drawings.

Figure 1:
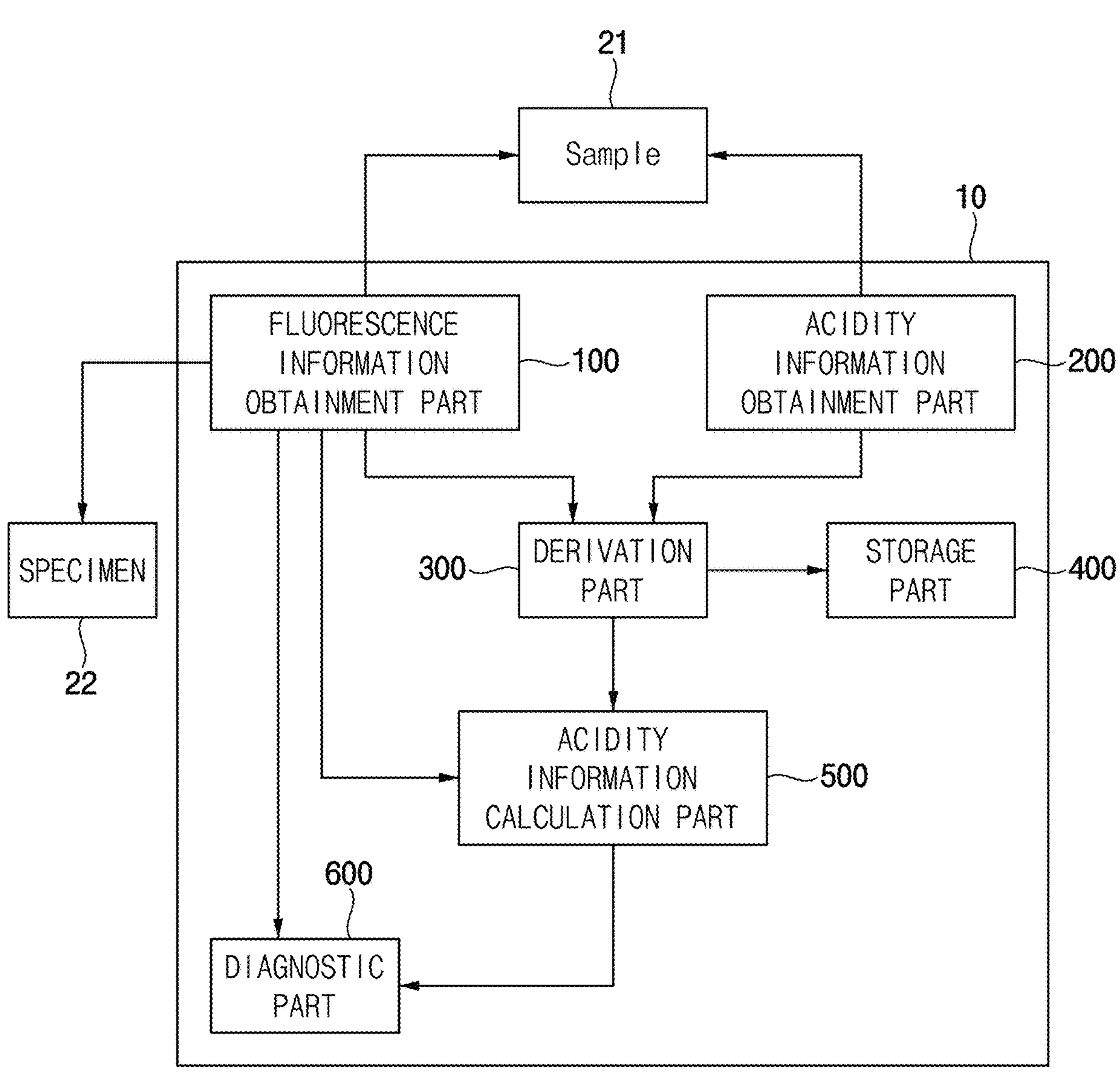
FIG. 1 is a block diagram illustrating a diagnosis system according to an example embodiment of the present invention.
Figure 2:
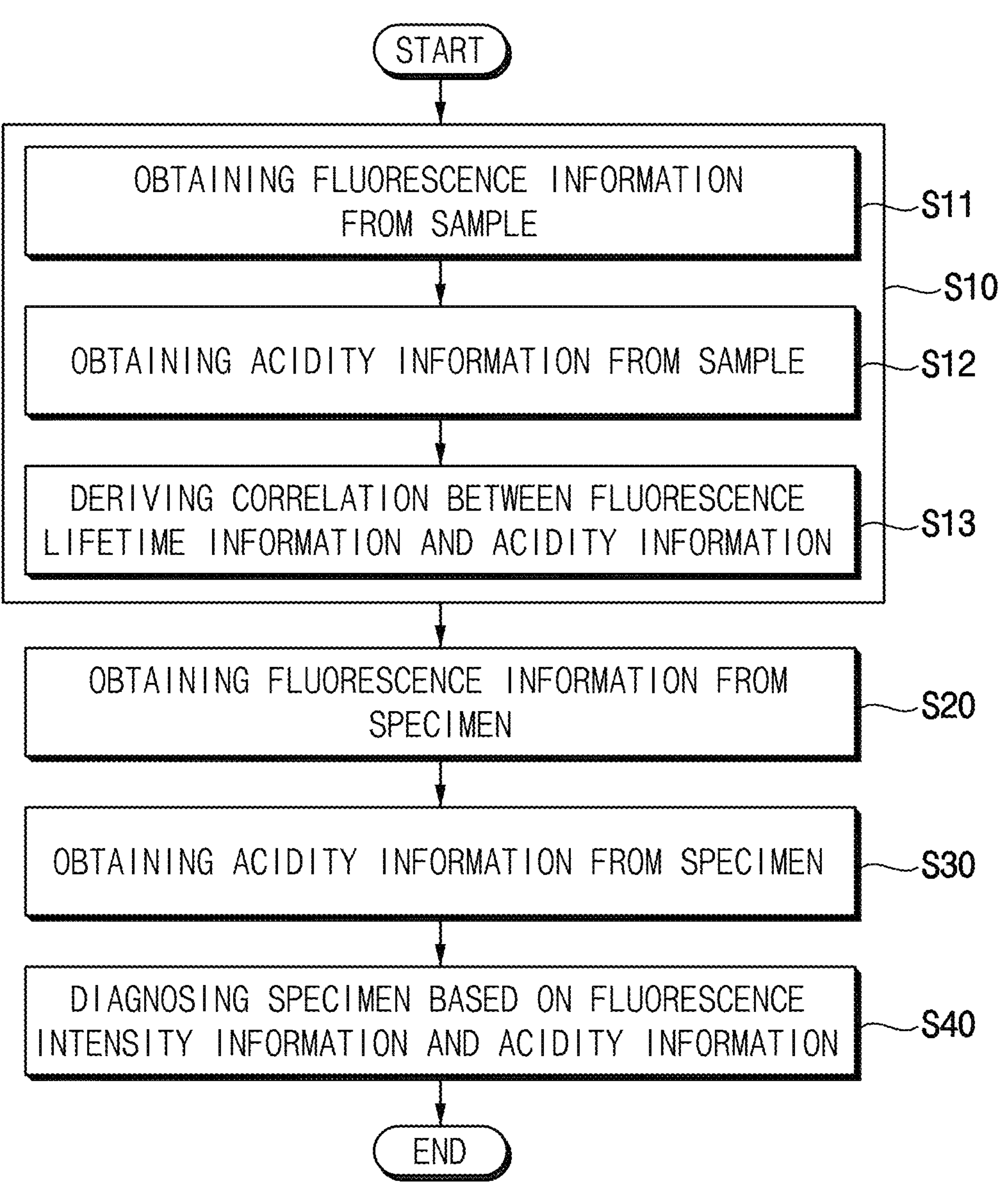
FIG. 2 is a flow chart illustrating a diagnosis method using the diagnosis system of FIG. 1.
Figure 3:
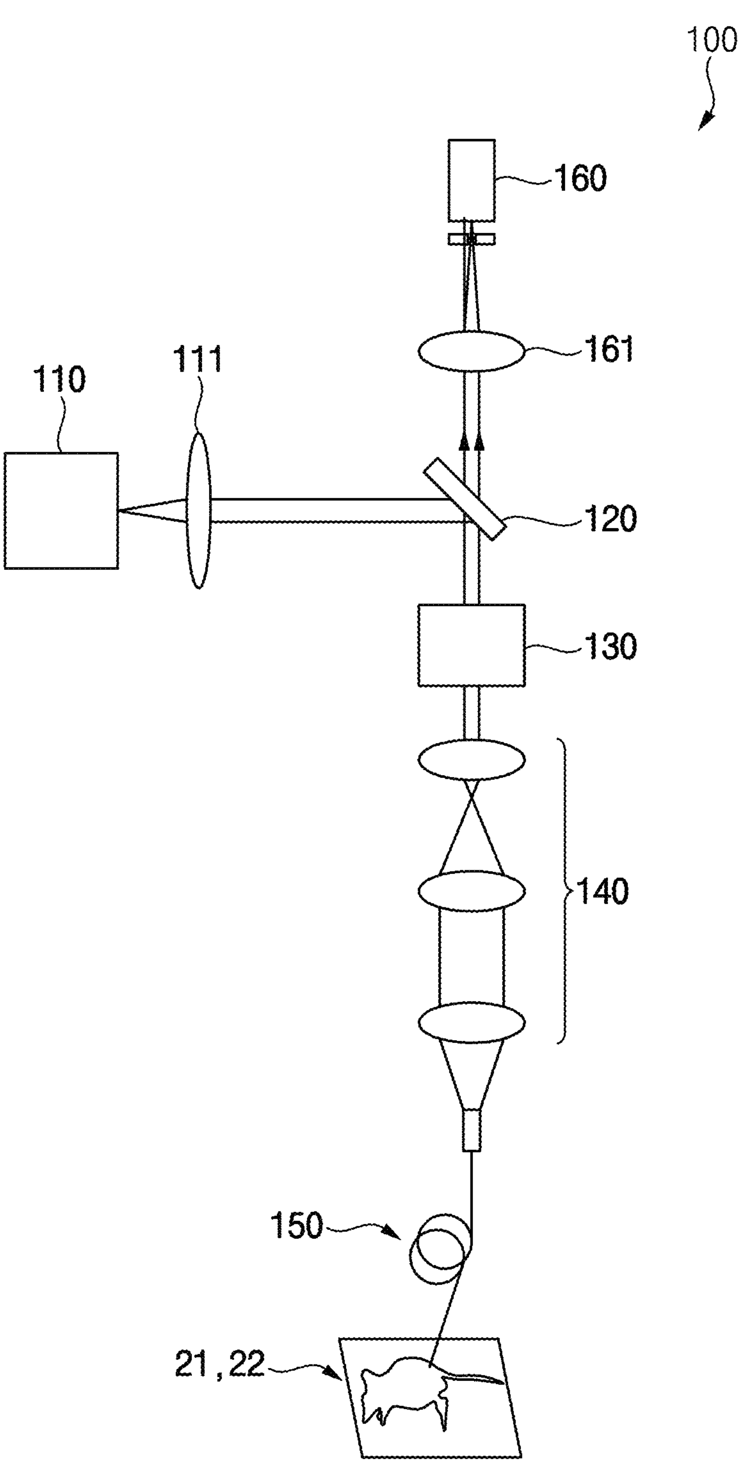
FIG. 3 is a schematic diagram illustrating a fluorescence information obtainment part of FIG. 1.
Figure 4:
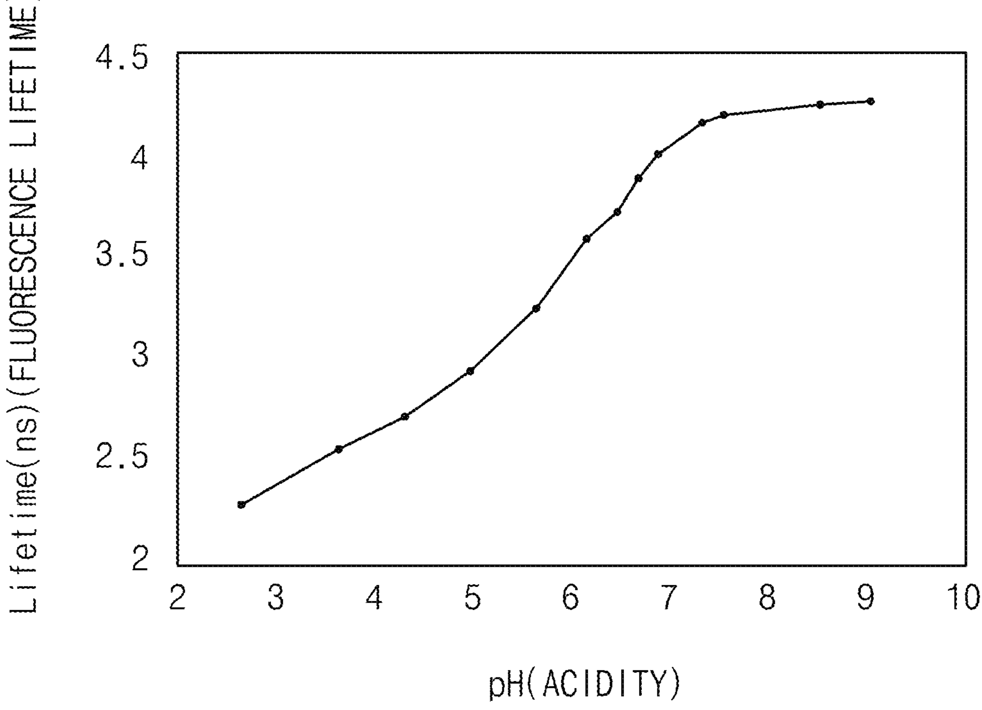
FIG. 4 is a graph showing a correlation between a fluorescence lifetime derived from a derivation part of FIG. 1 and acidity.

FIG. 1 is a block diagram illustrating a diagnosis system according to an example embodiment of the present invention. FIG. 2 is a flow chart illustrating a diagnosis method using the diagnosis system of FIG. 1. FIG. 3 is a schematic diagram illustrating a fluorescence information obtainment part of FIG. 1. FIG. 4 is a graph showing a correlation between a fluorescence lifetime derived from a derivation part of FIG. 1 and acidity.

Referring to FIG. 1, the diagnosis system 10 according to the present example embodiment includes a fluorescence information obtainment part 100, an acidity information obtainment part 200, a derivation part 300, a storage part 400, an acidity information calculation part 500 and a diagnostic part 600.

Hereinafter, referring to FIG. 1 and FIG. 2 together, the diagnosis system 10 and the diagnosis method using the diagnosis system 10 are explained at the same time.

In the diagnosis method, information on a correlation between fluorescence information and acidity information is stored (step S10).

Before diagnosing a specimen 22 subject to diagnosis, database is stored for various kinds of samples 21. Here, the stored database is the data on the correlation between the fluorescence information and the acidity information.

The specimen 22 may include a cancer cell, and an object of the diagnosis is the cancer diagnosis. Thus, sample 21 should include the cancer cell and the kinds of the samples 21 should be prepared variously.

For the samples 21 containing various types of cancer cells, data on the correlation between the fluorescence information and the acidity information is accumulated and stored. Then, necessary information is extracted for the specimen 22 requiring examination, and examination is performed on the specimen 22 using the stored data.

Here, the correlation is described as the correlation between the fluorescence information and the acidity information, but actually means the correlation between the fluorescence lifetime information and the acidity information.

For example, in storing the information on the correlation (step S10), first, the fluorescence information obtainment part 100 obtains fluorescence information from the sample 21 (step S11).

Here, the obtained fluorescence information is fluorescence intensity information and fluorescence lifetime information, and as an example, the fluorescence information obtainment part 100 may be a confocal scanning system in FIG. 3.

Referring to FIG. 3, the fluorescence information obtainment part 100 may be the confocal scanning system, and includes a laser generator 110, a light distributer 120, a scanner 130, a lens unit 140, a probe 150 and a detector 160.

The laser generator 110 generates a pulse laser and provides the pulse laser to the light distributer 120 through a first lens 111. The light distributer 120 provides the pulse laser toward the scanner 130.

The scanner 130 provides the pulse laser toward the sample 21 for scanning the sample 21, and the scanner 130 controls a focus of the laser provided to the sample 21 through the probe 150 or performs a focusing on a scanning position.

Then, the laser light detected from the sample 21 is provided to the detector 160 through a second lens 161, and the detector 160 analyzes the laser light and detects the fluorescence intensity information and the fluorescence lifetime information on the sample 21.

In addition, each of the fluorescence intensity information and the fluorescence lifetime information detected by the detector 160 is imaged and provided.

Compared to the conventional technology in which the required information, i.e., the diagnosis on the sample 21 or the specimen 22 is obtained based on the fluorescence intensity information, in the present example embodiment, the required information, i.e., the diagnosis on the sample 21 or the specimen 22 is obtained based on the fluorescence lifetime information in addition to the fluorescence intensity information.

In the present example embodiment, for obtaining the fluorescence lifetime information, the conventional technology in which the light signal obtained in the photo detector is passed through a filter (Gaussian low pass filter, GLPF) and an amplifier and then the signal is measured and restored in a digitizer and finally the signal is obtained, may be simplified.

In other words, the digitizer capable of sampling a frequency over 1 gigabyte is used and the filter and the amplifier are omitted, and the fluorescence lifetime is directly measured and obtained from the detected light.

Thus, the signal-to-noise (SNR) may be relatively decreased.

Accordingly, in obtaining the fluorescence information on the sample 21 using the fluorescence information obtainment part 100, as explained above, using the fluorescence information obtainment part 100 for various samples 21, the fluorescence intensity information and the fluorescence lifetime information are obtained as fluorescence information (step S11).

Further, in the present example embodiment, as an example of the fluorescence information obtainment part 100, the confocal scanning system is explained. However, the fluorescence information obtainment part 100 may be manufactured as a microscope type capable of diagnosing the sample 21 excised from tissue.

In addition, when the microscope type is manufactured, the acidity information obtainment part 200 is included together and the diagnosis system 10 may be performed as the microscope type.

The acidity information obtainment part 200 obtains the acidity information from the sample 21 (step S12). In an exemplary embodiment, the acidity information obtainment part 200 comprises a pH measurement device that directly measures pH of the sample 21 and outputs the measured pH as the first acidity information of the sample 21.

Here, the acidity information is degree of acidity or degree of acidity intensity of the sample, and is obtained with hydrogen ion index (pH).

The acidity information obtainment part 200 obtains the acidity information on the sample, based on the correlation between the acidity of the fluorescent contrast agent used for obtaining the fluorescence information and the fluorescence lifetime information among the fluorescence information.

The acidity information obtainment part 200 may obtain the acidity information by directly measuring pH of the sample 21, and here, the conventionally well-known acidity information measurement device may be used.

Accordingly, the fluorescence lifetime information and the fluorescence intensity information are obtained on each sample 21, as the fluorescence information, and the acidity information is obtained at the same time. Then, the derivation part 300 derives correlation between the fluorescence lifetime information and the acidity information on each sample 21 (step S13). In an exemplary embodiment, the derivation part 300 is implemented by a processor executing instructions stored in a memory, the instructions causing the derivation part 300 to: (i) receive, for each sample 21 of a plurality of samples corresponding to a plurality of cancer cell types, paired data points of the first fluorescence lifetime information and the first acidity information; (ii) for each cancer cell type, derive a correlation equation that relates the first fluorescence lifetime information to the first acidity information for that cancer cell type, as illustrated in FIG. 4; and (iii) output the correlation equation, associated with the corresponding cancer cell type, to the storage part 400.

Figure 5:
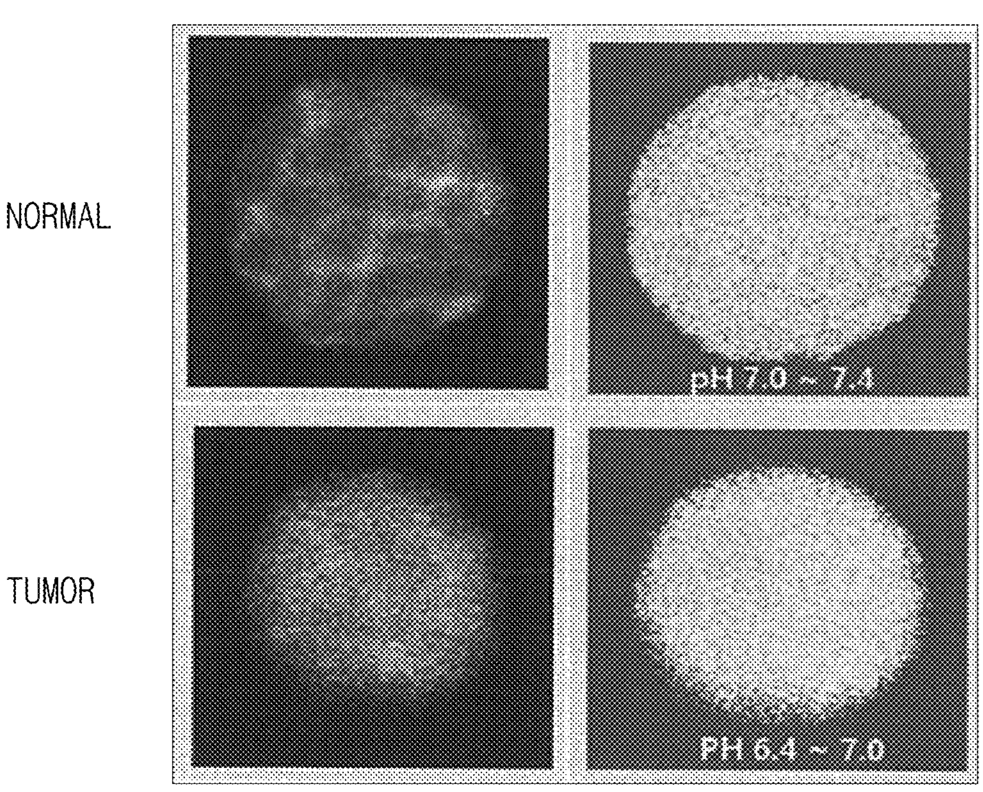
FIG. 5 is an image showing results of the diagnosis for specimens using the diagnosis system of FIG. 1.

As illustrated in FIG. 5, the correlation between the fluorescence lifetime information and acidity information may be derived as a graph.

For example, as explained above, after the acidity information obtainment part 200 measures the acidity and fluorescence lifetime information of fluorescence contrast agent used in obtaining the fluorescence information and a correlation equation of the acidity and the fluorescence lifetime information is obtained, the acidity of the sample 21 is obtained, and based on the obtained acidity, the correlation between the fluorescence lifetime information and the acidity information is obtained.

In FIG. 4, the acidity of the sample increases as the fluorescence lifetime increases, and when the acidity is over 7, the fluorescence lifetime is maintained uniformly.

Accordingly, the correlation between the fluorescence lifetime information and the acidity information is obtained for each sample 21, and then the correlation is stored in the storage part 400. In an exemplary embodiment, the storage part 400 comprises a memory that stores, for each cancer cell type, the correlation equation output by the derivation part 300 in association with the corresponding cancer cell type, such that the correlation equation for a given cancer cell type can be retrieved from the storage part 400 based on the cancer cell type.

Then, the diagnosis for the actual specimen 22 is performed. Here, the specimen 22 may be obtained from the patient, or if the obtainment from a patient is difficult, diagnosis may be performed on the patient where the sample 22 is located for non-invasive diagnosis.

Thus, in the fluorescence information obtainment part 100 obtains the fluorescence information on the specimen 22, using the pulse laser (step S20). Here, the obtainment of the fluorescence information on the specimen 22 is substantially same as that of the fluorescence information on the sample 21 as explained in step S11.

Then, the acidity information calculation part 500 calculates the acidity information on the specimen 22, based on the correlation between the fluorescence lifetime information and the acidity information stored in the storage part 400 (step S30). In an exemplary embodiment, the acidity information calculation part 500 is implemented by a processor executing instructions stored in a memory, the instructions causing the acidity information calculation part 500 to: (i) receive, from the fluorescence information obtainment part 100, the second fluorescence lifetime information measured from the specimen 22; (ii) retrieve, from the storage part 400, the correlation equation associated with the cancer cell type of the sample 21 corresponding to the specimen 22; (iii) apply the second fluorescence lifetime information to the retrieved correlation equation to compute the second acidity information of the specimen 22; and (iv) provide the computed second acidity information of the specimen 22 to the diagnostic part 600.

In the storage part 400, the correlation between the fluorescence information and the acidity information for various samples 21, and thus, the acidity information for the specimen 22 may be calculated based on the stored correlation on the sample 21 related to the specimen 22 to be diagnosed.

For example, when the specimen 22 to be diagnosed is a stomach cancer specimen, the stored correlation between the fluorescence lifetime information and the acidity information through the stomach cancer sample may be used.

Accordingly, when the acidity information on the specimen 22 is calculated, the diagnostic part 600 performs diagnosis on the specimen 22 based on the fluorescence information and the acidity information (step S40). In an exemplary embodiment, the diagnostic part 600 is implemented by a processor executing instructions stored in a memory, the instructions causing the diagnostic part 600 to: (i) receive the second fluorescence intensity information measured from the specimen 22 by the fluorescence information obtainment part 100 and the calculated second acidity information of the specimen 22 from the acidity information calculation part 500; (ii) compare the calculated second acidity information of the specimen 22 to one or more reference pH ranges associated with diagnostic categories, including the normal-region range of pH 7.0-7.4 and the tumor-region range of pH 6.4-7.0 and (iii) output a diagnosis of the specimen 22 as a normal area or a tumor area based on said comparison and on the second fluorescence intensity information.

Here, the diagnosis of the specimen is not performed simply based on the fluorescence intensity information, but the diagnosis of the specimen is performed based on the fluorescence intensity information and the acidity information at the same time, and thus the diagnosis of the specimen may be performed more accurately.

FIG. 5 is an image showing results of the diagnosis for specimens using the diagnosis system of FIG. 1.

Referring to FIG. 5, when the diagnosis of the specimen according to the present example embodiment is performed, it may be diagnosed as a normal area if the actual acidity information pH is in a range of 7.07.4, and it may be diagnosed as a tumor area if the actual acidity information pH is in a range of 6.47.0. Accordingly, the acidity information and the fluorescence intensity information are used at the same time, and the diagnosis may be performed more accurately.

According to the present embodiment, cancer diagnosis may be performed based on a sample by simultaneously using fluorescence information, especially fluorescence intensity information and acidity information, and thus the accuracy of cancer diagnosis may be improved compared to cancer diagnosis techniques that simply use fluorescence intensity information.

Here, considering the difficulty in obtaining acidity information for samples using a non-invasive method, various types of cancer cells that are subject to diagnosis are sampled and information on the correlation between fluorescence lifetime information and acidity information was collected in each sample, and in the case of actual samples, only fluorescence lifetime information is obtained and the acidity information is calculated based on this, and thus using the non-invasive method, user's convenience may be improved and cancer diagnosis may be performed more accurately.

In addition, the fluorescence information, that is, the fluorescence lifetime information and the fluorescence intensity information, are acquired using a confocal scanning system using a pulse laser, and thus the accuracy of information obtained may be improved, and non-invasive information acquisition may be possible, improving user's convenience.

In obtaining the fluorescence lifetime information, conventionally the optical signal obtained from the optical detector is electrically passed through a filter (GLPF, Gaussian low pass filter) and amplifier and then the signal is measured and restored at the digitizer to simplify acquisition. However, in the present example embodiment, by using the digitizer that can sample a relatively high frequency of 1 gigabyte or more, the fluorescence lifetime may be obtained by measuring the fluorescence lifetime directly from the detected light, omitting filters and amplifiers, and thus signal-to-noise ratio (SNR) may be decreased.

Having described exemplary embodiments of the present invention, it is further noted that it is readily apparent to those of reasonable skill in the art that various modifications may be made without departing from the spirit and scope of the invention which is defined by the metes and bounds of the appended claims.

What is claimed is:

1. A diagnosis system comprising:

a fluorescence information obtainment part configured to obtain a first fluorescence lifetime information and a first fluorescence intensity information from each of samples and to obtain a second fluorescence lifetime information and a second fluorescence intensity information from a specimen subject to diagnosis;

an acidity information obtainment part configured to obtain a first acidity information from each of the samples;

a derivation part configured to derive a correlation between the first fluorescence lifetime information and the first acidity information for each of the samples;

an acidity information calculation part configured to calculate a second acidity information of the specimen based on the second fluorescence lifetime information obtained from the specimen, using the correlation; and a diagnostic part configured to perform cancer diagnosis on the specimen based on the second fluorescence lifetime information obtained from the specimen and the calculated second acidity information, wherein the acidity information calculation part is configured to obtain the first acidity information from each of the samples, based on the correlation between acidity of fluorescent contrast agent and the first fluorescence lifetime information, wherein the fluorescent contrast agent is used to obtain the first fluorescence lifetime information and the first fluorescence intensity information of each of the samples, wherein the acidity information calculation part is configured to calculate the second acidity information of the specimen, using the correlation on the sample corresponding to the specimen among the correlations on each of the samples which are derived by the derivation part, wherein the sample is cancer cells of each type that are the target of diagnosis, wherein the derivation part is configured to derive the correlation between the first fluorescence lifetime information for each type cancer cell and the first acidity information.

* * * * *